(12) United States Patent
Yamamoto et al.

(10) Patent No.: US 8,709,614 B2
(45) Date of Patent: Apr. 29, 2014

(54) ORGANIC METAL COMPLEX AND ITS USE IN ORGANIC ELECTROLUMINESCENT DEVICE

(75) Inventors: Toshihiro Yamamoto, Kitakyushu (JP); Takahiro Kai, Kitakyushu (JP); Masaki Komori, Kitakyushu (JP); Hiroshi Miyazaki, Kitakyushu (JP)

(73) Assignee: Nippon Steel & Sumikin Chemical Co., Ltd., Tokyo (JP)

( * ) Notice: Subject to any disclaimer, the term of this patent is extended or adjusted under 35 U.S.C. 154(b) by 1565 days.

(21) Appl. No.: 11/921,001

(22) PCT Filed: Jun. 5, 2006

(86) PCT No.: PCT/JP2006/311203
§ 371 (c)(1),
(2), (4) Date: Jan. 22, 2008

(87) PCT Pub. No.: WO2006/132173
PCT Pub. Date: Dec. 14, 2006

(65) Prior Publication Data
US 2009/0026923 A1    Jan. 29, 2009

(30) Foreign Application Priority Data
Jun. 7, 2005    (JP) .................................. 2005-166581

(51) Int. Cl.
*H01L 51/54*    (2006.01)

(52) U.S. Cl.
USPC ........... 428/690; 428/917; 313/504; 313/506; 252/301.16; 252/301.27; 257/40; 257/102; 257/E51.043; 548/108

(58) Field of Classification Search
USPC .................................................. 257/E51.043
See application file for complete search history.

(56) References Cited

U.S. PATENT DOCUMENTS

| | | | |
|---|---|---|---|
| 6,097,147 A | 8/2000 | Baldo et al. | |
| 6,358,634 B1 | 3/2002 | Igarashi et al. | |
| 2002/0034655 A1 | 3/2002 | Watanabe et al. | |
| 2003/0218418 A9* | 11/2003 | Sato et al. | 313/504 |
| 2003/0230738 A1* | 12/2003 | Thoms et al. | 252/301.16 |
| 2004/0124769 A1* | 7/2004 | Ise et al. | 313/504 |
| 2007/0134514 A1* | 6/2007 | Kondakov et al. | 428/690 |

FOREIGN PATENT DOCUMENTS

| | | |
|---|---|---|
| JP | 2000-302754 A | 10/2000 |
| JP | 2001-313178 A | 11/2001 |
| JP | 2002-305083 A | 10/2002 |
| JP | 2002-352957 A | 12/2002 |
| JP | 2003-123972 A | 4/2003 |
| JP | 2003-515897 A | 5/2003 |
| JP | 2004-067658 A | 3/2004 |

OTHER PUBLICATIONS

Wang et al., "Novel bis(8-hydroxyquinoline)phenolato-aluminum complexes for organic light-emitting diodes", Synthetic Metals, vol. 131, pp. 1-5 (2002).

* cited by examiner

*Primary Examiner* — Michael H Wilson
(74) *Attorney, Agent, or Firm* — Birch, Stewart, Kolasch & Birch, LLP

(57) ABSTRACT

Disclosed are an organic electroluminescent device (organic EL device) that is improved in luminous efficiency and fully assured of driving stability and has a simple structure and an organic metal complex suitable therefor. The organic metal complex is represented by the following general formula (I)

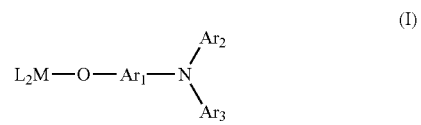

wherein $Ar_1$ denotes an aromatic hydrocarbon group or a heteroaromatic group and may have substituents, $Ar_2$ and $Ar_3$ respectively denote an aromatic hydrocarbon group or a heteroaromatic group and may have substituents, M denotes a trivalent metal, and L denotes an arylate ligand containing a hetero ring having at least one nitrogen atom capable of coordinating M. This organic metal complex, along with a phosphorescent dopant, is suitable for a material constituting the light-emitting layer of an organic EL device.

4 Claims, 1 Drawing Sheet

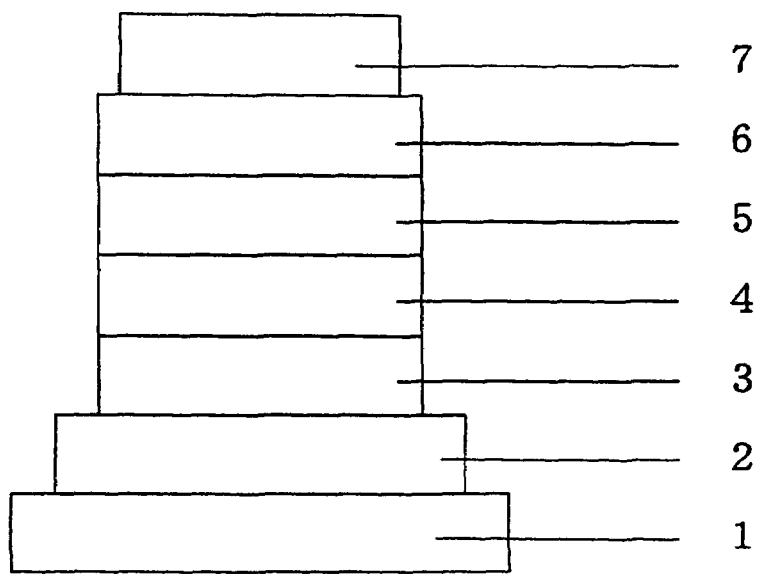

ORGANIC METAL COMPLEX AND ITS USE IN ORGANIC ELECTROLUMINESCENT DEVICE

FIELD OF TECHNOLOGY

This invention relates to an organic metal complex and an organic electroluminescent device (hereinafter referred to as an organic EL device) using the same.

BACKGROUND TECHNOLOGY

An organic electroluminescent device of the simplest structure is generally the one constituted of a light-emitting layer sandwiched between a pair of counter electrodes. Upon application of an electric voltage between the electrodes of an organic EL device, electrons injected from the cathode and holes injected from the anode recombine in the light-emitting layer and the energy level after recombination returns from the conduction band to the valence band with emission of light; it is the phenomenon of this emission of light that is utilized by an organic EL device.

Organic EL devices and organic EL materials used therefore are known in a large number of documents. The use of phosphorescence instead of fluorescence has been investigated in an attempt to enhance the luminous efficiency of an organic EL device. Namely, a device utilizing emission of light from the triplet excited state is expected to perform at a higher efficiency, approximately three times the efficiency of a conventional device utilizing fluorescence (singlet). Numerous developmental works on phosphorescent dopants have been under way to achieve this end.

The following patent documents are known in relation to this invention.

Patent document 1: JP2003-515897 A
Patent document 2: JP2001-313178 A
Patent document 3: JP2002-305083 A
Patent document 4: JP2002-352957 A The patent document 1 describes complexes represented by $L_2MX$ as phosphorescent dopants for use in organic EL devices. In a preferable example of $L_2MX$ cited in the document, L is a substituted benzoxazole, M is iridium, and X is a ligand functioning as a trap for holes. The host material proposed for use in the light-emitting layer is a carbazole compound and 4,4'-N,N-dicarbazoylbiphenyl (CBP) is mentioned to be particularly preferable.

The patent document 2 discloses an organic EL device comprising a light-emitting layer in which 0.5 to 8 wt % of a phosphorescent iridium complex is incorporated. Here, tris (2-phenylpyridine)iridium or Ir(ppy)3 is cited as a preferable iridium complex and CBP as a preferable host material for the light-emitting layer.

A host material containing no phosphorescent dopant is useful as a material for a fluorescent EL device. However, a phosphorescent EL device has an advantage of enhanced luminous efficiency as mentioned above and, in the fabrication of a phosphorescent EL device, the compatibility of a host material with a phosphorescent dopant becomes an important factor. The aforementioned CBP has a property of facilitating the flow of holes and obstructing the flow of electrons and the problem with the use of CBP is that the balance of electron and hole injection is destroyed and excessive holes flow out to the electron transporting-layer side and, as a result, the luminous efficiency from Ir(ppy)3 drops.

The patent document 3 discloses an organic EL device which utilizes phosphorescence and comprises in its light-emitting layer an organic metal complex (1) containing a metal of Groups 7 to 11 in the periodic table and an organic metal complex (2) represented by $[-A-B-O-]_{n-j}M-L_j$ wherein A is a heterocycle such as a diazole, B is a ring compound like benzene, M is a metal of Groups 1 to 3 or Groups 12 and 13 in the periodic table, L is a substituent, and n is a valence of M. Examples cited for the organic metal complex (1) are iridium complexes such as Ir(ppy)3 and platinum complexes. The document states that a light-emitting layer comprising a conventional combination of an iridium complex such as Ir(ppy)3 and a host material such as CBP has problems of a decrease in the stability of the film structure as CBP tends to crystallize readily and of the driving stability and the document proposes to use the organic metal complex (2) as a host material. However, in spite of the fact that the number of the organic metal complexes (2) represented by the aforementioned formula is practically infinite because the substituent L can be chosen arbitrarily from an infinite variety of candidates, only the following two complexes are cited in the examples for concrete use of the organic metal complex (2): in one complex, A is a phenyl-substituted bezothiazole ring, B is a benzene ring, M is zinc, n is 2, and j is 0; in the other complex, A is a thiazole ring, B is a benzene ring, M is beryllium, n is 2, and j is 0.

The patent document 4 discloses a phosphorescent organic EL device wherein the light-emitting layer comprises a conventional iridium complex such as Ir(ppy)3 or platinum complex as a dopant and a compound containing an oxadiazole or triazole group as a host material and claims that such use of a compound containing an oxadiazole or triazole group makes it possible to form a light-emitting layer by a wet process and, as a result, the host material mixes sufficiently with the dopant and light of high brightness is emitted with minimal fluctuation. However, none of the oxadiazole or triazole compounds disclosed as host materials contains a metal and no description is given to teach that a host material is metal complex. The compound cited as a triazole or 3-phenyl-4-(1'-naphthyl)-5-phenyl-1,2,4-triazole (TAZ) has a property of facilitating the flow of electrons and obstructing the flow of holes and this shifts the light-emitting range to the side of the hole-transporting layer. Therefore, it is conceivable that the luminous efficiency from Ir(ppy)3 may drop depending upon the compatibility of Ir(ppy)3 with the material used for the hole-transporting layer. For example, 4,4'-bis(N-(1-naphthyl)-N-phenylamino)biphenyl (NPB) which is used most frequently in the hole-transporting layer on account of its excellent performance, high reliability, and long lifetime is poorly compatible with Ir(ppy)3 and the use of this compound raises a problem in that the transition of energy occurs from Ir(ppy)3 to NPB with the resultant drop in luminous efficiency.

The use of a material like 4,4'-bis(N,N'-(3-tolyl)amino)-3, 3'-dimethylbiphenyl (HMTPD) to which the transition of energy from Ir(ppy)3 does not occur for the hole-transporting layer is conceivable as a means to solve the aforementioned problem, but this cannot be said to offer an excellent means from the viewpoint of luminous efficiency.

DISCLOSURE OF THE INVENTION

Problems to be Solved by This Invention

In application of an organic EL device to a display device such as a flat panel display, it is necessary to improve both the luminous efficiency and the driving stability of the device. Under the aforementioned circumstances, an object of this invention is to provide an organic EL device which performs at high efficiency with excellent driving stability and to provide an organic metal complex suitable for the said device.

Means to Solve the Problems

After intensive studies, the inventors of this invention have found that optimizing the balance of holes and electrons in the light-emitting layer can solve the aforementioned problems and completed this invention. The finding indicates that introduction of a triphenylamine skeleton having a high hole-transporting ability to a metal complex improves the hole-transporting ability of the complex itself and, as a result, the balance of electrons and holes is optimized, the light-emitting range can be broadened, and the luminous efficiency can be enhanced.

Accordingly, this invention relates to an organic metal complex represented by the following general formula (I) for use in an organic EL device;

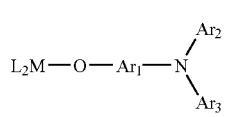
(I)

in formula (I), $Ar_1$ denotes a divalent aromatic hydrocarbon group or a divalent heteroaromatic group and may have substituents, $Ar_2$ and $Ar_3$ respectively denote an aromatic hydrocarbon group or a heteroaromatic group and may have substituents and $Ar_2$ and $Ar_3$ never link together to form a ring, M denotes a trivalent metal, and L denotes an arylate or heteroarylate ligand containing a heterocyclic group having at least one nitrogen atom capable of coordinating M and may have substituents.

Examples of L in general formula (I) include ligands represented by the following general formulas (II) to (IV).

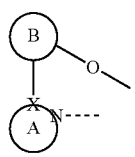
(II)

In general formula (II), ring A is a nitrogen-containing heterocyclic ring and may have substituents, ring B is an aromatic hydrocarbon ring or a heteroaromatic ring and may have substituents, two or more substituents located respectively on rings A and B may link together to form a ring, and X is a carbon or nitrogen atom.

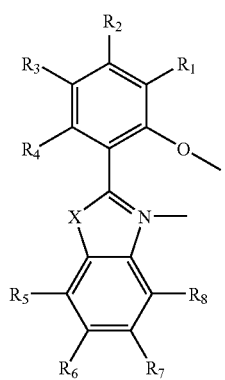
(III)

In general formula (III), the groups $R_1$ to $R_8$ respectively denote a hydrogen atom or an arbitrary substituent, substituents located adjacently may link together to form a ring, and X is an oxygen or sulfur atom.

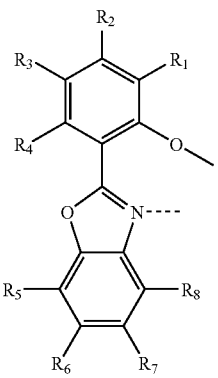
(IV)

In general formula (IV), the groups $R_1$ to $R_8$ respectively denote a hydrogen atom, halogen atom, alkyl group, aralkyl group, alkenyl group, alkynyl group, cyano group, dialkylamino group, diarylamino group, diaralkylamino group, amino group, nitro group, acyl group, alkoxycarbonyl group, carboxyl group, alkoxyl group, alkylsulfonyl group, haloalkyl group, hydroxyl group, amide group, aromatic hydrocarbon group which may have substituents, and heteroaromatic group which may have substituents.

Examples of $Ar_1$ in general formula (I) include various groups represented by the following general formula (IX);

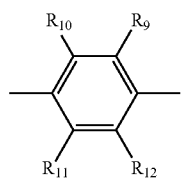
(IX)

in general formula (IX), the groups $R_9$ to $R_{12}$ independently denote a hydrogen atom, halogen atom, alkyl group, aralkyl group, alkenyl group, alkynyl group, cyano group, dialkylamino group, diarylamino group, diaralkylamino group, amino group, nitro group, acyl group, alkoxycarbonyl group, carboxyl group, alkoxyl group, alkylsulfonyl group, haloalkyl group, hydroxyl group, amide group, aromatic hydrocarbon group which may have substituents, and heteroaromatic group which may have substituents and, where the aromatic hydrocarbon group or heteroaromatic group has substituents, those substituents which are located adjacently may link together to form a ring.

Examples of $Ar_2$ and $Ar_3$ in general formula (I) include various groups represented by the following general formula (X);

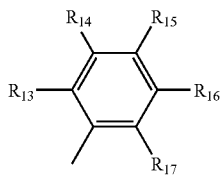
(X)

the groups $R_{13}$ to $R_{17}$ independently denote a hydrogen atom, halogen atom, alkyl group, aralkyl group, alkenyl group, alkynyl group, cyano group, dialkylamino group, diarylamino group, diaralkylamino group, amino group, nitro group, acyl group, alkoxycarbonyl group, carboxyl group, alkoxyl group, alkylsulfonyl group, haloalkyl group, hydroxyl group, amide group, aromatic hydrocarbon group which may have substituents, and heteroaromatic group which may have substituents and, where the aromatic hydrocarbon group or heteroaromatic group has substituents, those substituents which are located adjacently may link together to form a ring.

Furthermore, this invention relates to an organic electroluminescent device comprising an organic layer containing the aforementioned organic metal complex. A phosphorescent organic EL device is obtained when its light-emitting layer comprises a phosphorescent dopant in addition to the said organic metal complex.

This invention is described further below.

The organic metal complex of this invention is represented by the aforementioned general formula (I). In general formula (I), L, $Ar_1$, $Ar_2$, and $Ar_3$ are preferably the groups respectively represented by general formulas (II), (III), (IV), (IX), and (X). The groups $R_1$ to $R_8$ in general formulas (III) and (IV) are as defined earlier, but they are preferably hydrogen atoms, alkyl groups of 1 to 6 carbon atoms, alkoxyl groups of 1 to 6 carbon atoms, and phenyl groups which may be substituted with alkyl groups of 1 to 6 carbon atoms.

The group $Ar_1$ is as defined earlier and examples of $Ar_1$ as a divalent aromatic hydrocarbon group which may have substituents or a divalent heteroaromatic group which may have substituents preferably include phenylene, naphthylene, and pyridilene groups, more preferably, phenylene groups and phenylene groups substituted with alkyl groups of 1 to 6 carbon atoms.

The groups $Ar_2$ and $Ar_3$ are as defined earlier and examples of $Ar_2$ or $Ar_3$ as an aromatic group which may have substituents preferably include phenyl, naphthyl, acenaphthyl, and anthryl groups, more preferably, phenyl and naphthyl groups. Examples of $Ar_2$ or $Ar_3$ as a heteroaromatic group which may have substituents preferably include pyridyl, quinolyl, thienyl, carbozolyl, indolyl, and furyl groups, preferably pyridyl and quinolyl groups. In the case where the aromatic hydrocarbon group or the heteroaromatic group has substituents, such substituents include lower alkyl groups of 1 to 6 carbon atoms, lower alkoxy groups of 1 to 6 carbon atoms, phenoxy groups, methylphenyloxy groups, benzyloxy groups, phenyl groups, naphthyl groups, and dimethylamino groups.

The groups $Ar_1$, $Ar_2$, and $Ar_3$ are respectively linked to N to form a triarylamine structure. It is this triarylamine structure that certain kinds of hole-transporting organic compounds possess and this fact helps one understand what $Ar_1$, $Ar_2$, and $Ar_3$ groups are preferable for hole-transporting organic compounds. A large number of hole-transporting organic compounds of this kind are described in the patent documents 1 to 4.

The symbol M stands for a trivalent metal and aluminum, gallium, and indium are preferable as such trivalent metals.

In general formula (I), L is linked to metal M through O (oxygen atom) and, in addition, L has a hetero ring containing a ring hetero atom capable of coordinating M. Furthermore, the aforementioned O is directly linked to a ring carbon atom of an aromatic ring and the hetero atom capable of coordinating M exists as a ring atom. Thus, both the O linked to M and the hetero atom coordinated to M exist close to each other. The hetero atom is as defined earlier, but it is preferably nitrogen here. It is allowable for L to have a hetero atom other than the one capable of coordinating M and, in such a case, these hetero atoms may be identical with or different from each other although L can be synthesized easily and advantageously when they are identical. However, this matter is not directly related to the usage of organic EL materials.

Preferable examples of L include ligands represented by general formulas (II), (III), and (IV).

In general formula (II), ring A contains a hetero atom capable of coordinating M while ring B contains a ring carbon atom which is linked to O. Rings A and B may have other hetero atoms or substituents. X is as defined above and it is preferably C (carbon atom).

Some of the groups represented by general formula (II) are described in the patent document 3. The group L is preferably represented by general formula (III), more preferably by general formula (IV).

In general formula (II), ring A is preferably a five- or six-membered nitrogen-containing hetero ring which may have substituents and this hetero ring may be condensed with one or two five- or six-membered aromatic hydrocarbon or hetero rings. The condensed rings thus formed may have the aforementioned substituents. On the other hand, ring B is preferably a six-membered aromatic hydrocarbon or heteroaromatic ring which may have substituents and this ring may be condensed with one or two five- or six-membered aromatic hydrocarbon or hetero rings. Likewise, the condensed rings thus formed may have the aforementioned substituents.

Concretely, ring A is preferably constituted of any of the following compounds which may have substituents; ring compounds such as diazole, thiazole, oxazole, thiadiazole, oxadiazole, triazole, pyridine, diazine, and triazine and the condensation products thereof with benzene such as benzodiazole, benzothiazole, benzothiadizole, benzoxadiazole, benzotriazole, quinoline, isoquinoline, benzodiazine, and benzotriazine. Ring B is preferably constituted of benzene, pyridine, diazine, triazine, and the condensation products thereof with benzene and ring B may have substituents.

In general formula (IV), the groups $R_1$ to $R_8$ are as defined above, but they are preferably hydrogen atoms, alkyl groups of 1 to 6 carbon atoms, or phenyl groups which may be substituted with alkyl groups of 1 to 6 carbon atoms.

The organic metal complex of this invention can be prepared by a known method. For example, a trialkoxide of metal M such as an aluminum trialkoxide is reacted with a compound having both a phenolic ring and a hetero ring such as 2-(2-hydroxyphenyl)benzoxazole to give a complex as an intermediate and the intermediate is reacted with a triarylamine type phenolic compound such as 4-diphenylaminophenol.

The aforementioned reactions can be expressed by chemical formulas as follows. The reaction of a trialkoxide of metal M or M(OR)$_3$ with a compound having both a phenolic ring and a hetero ring such as 2-(2-hydroxyphenyl)benzoxazole gives a complex represented by general formula (XI) as an intermediate, and the intermediate is then reacted with a compound represented by $Ar_2Ar_3N$—$Ar_1$-OH.

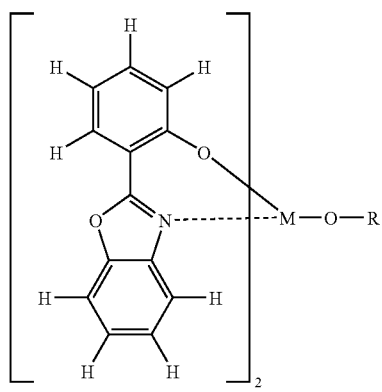

(XI)

Examples of the organic metal complex of this invention are shown below, but this invention is not limited to these examples.

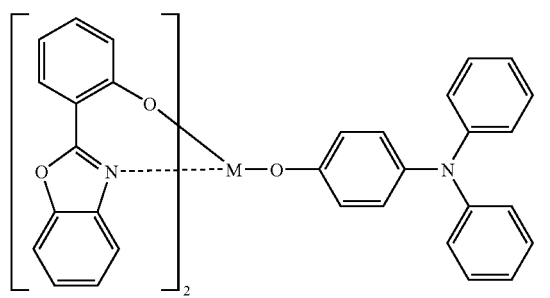
1
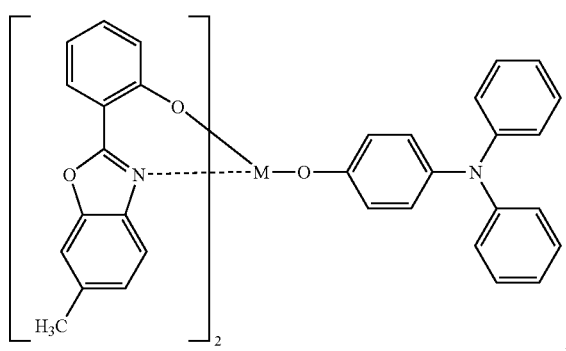
2
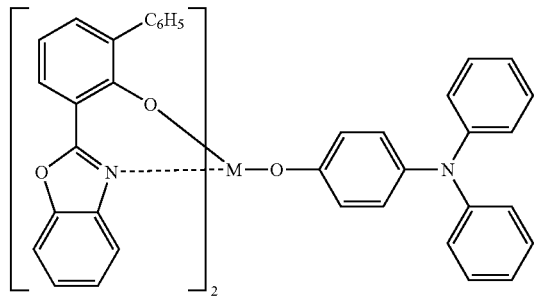
3
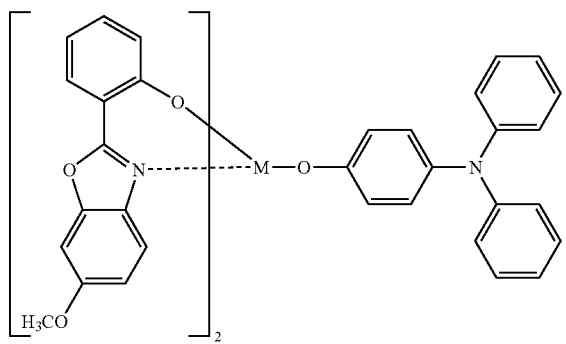
4
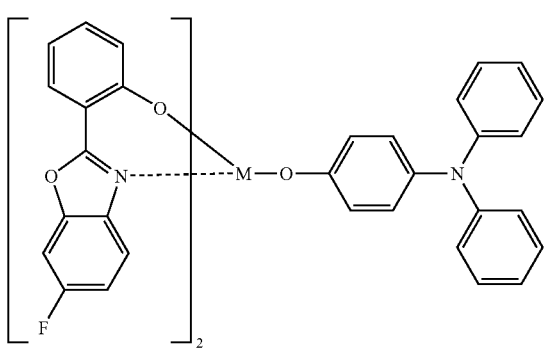
5
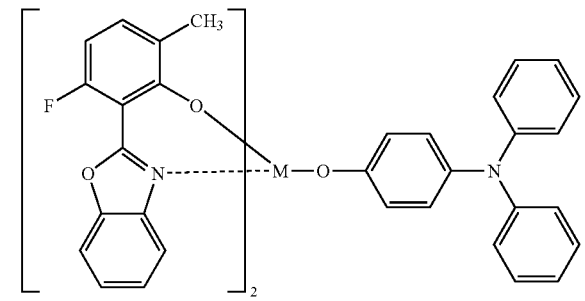
6
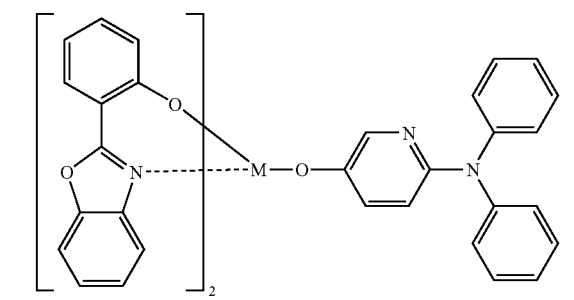
7
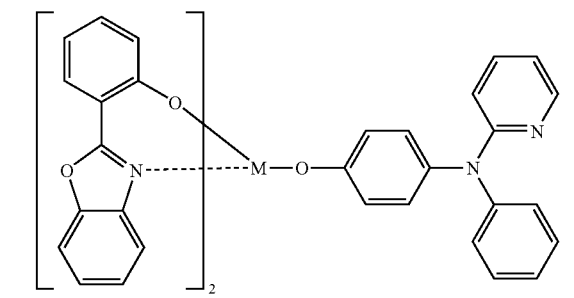
8
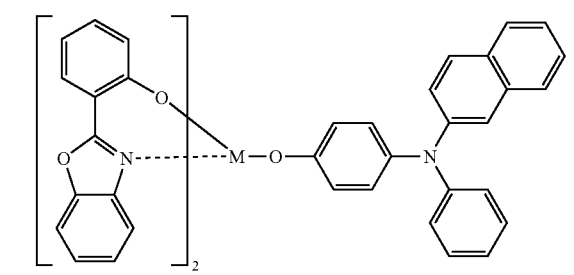
9
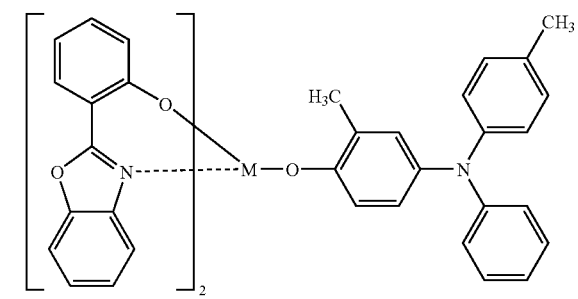
10

-continued

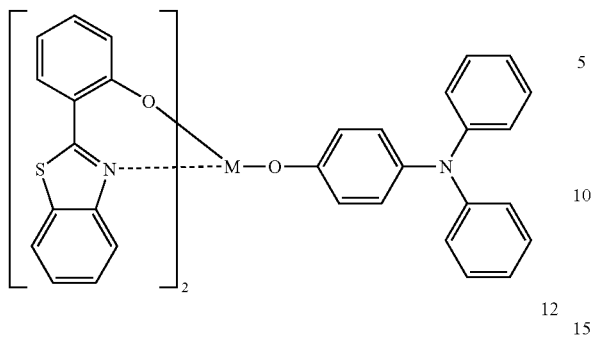

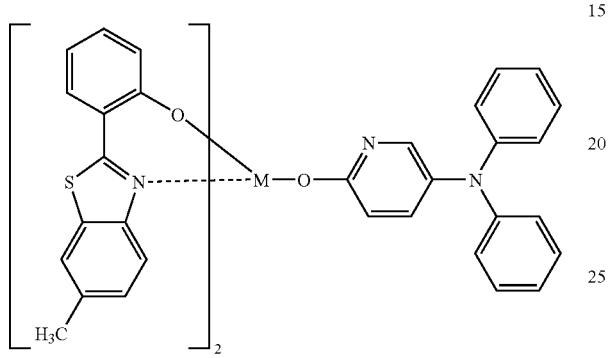

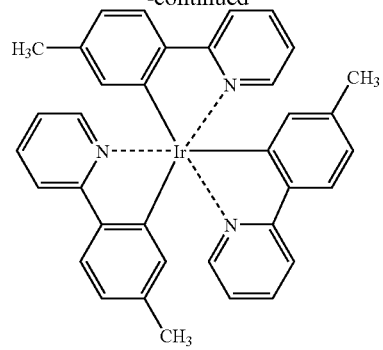

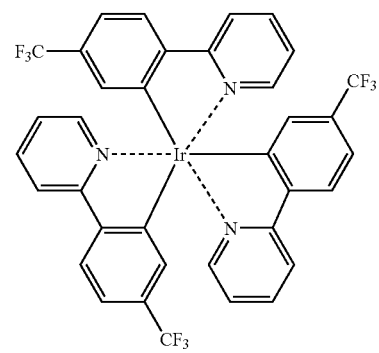

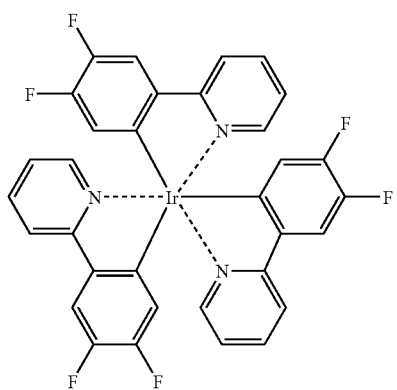

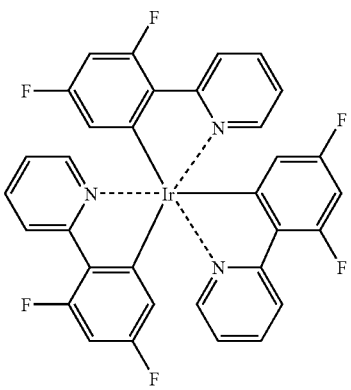

An organic EL device fabricated from the metal organic complex of this invention is described next. In the organic EL device of this invention, an anode, a cathode, and organic layers sandwiched between the electrodes are provided on a substrate and at least one of the organic layers comprises the said metal organic complex. The organic layer comprising the organic metal complex of this invention is suitable for use in a light-emitting layer, especially, in a light-emitting layer containing a phosphorescent dopant. In a case like this, it is preferable that the organic metal complex of this invention is the principal component of the light-emitting layer and it is particularly desirable that the light-emitting layer comprises the organic metal complex as a host material and the host material is doped with a phosphorescent dopant.

Examples of the materials suitable for phosphorescent dopants include organic metal complexes containing at least one metal selected from ruthenium, rhodium, palladium, silver, rhenium, osmium, iridium, platinum, and gold. Such organic metal complexes are known in the aforementioned patent documents and elsewhere and any of them can be selected for use.

Preferable phosphorescent dopants include organic metal complexes containing a noble metal element as the central metal; for example, Ir(ppy)3, Ir(bt)2·acac3, and PtOEt3. Examples of these noble metal complexes are shown below, but the phosphorescent dopants useful for this invention are not limited to these compounds.

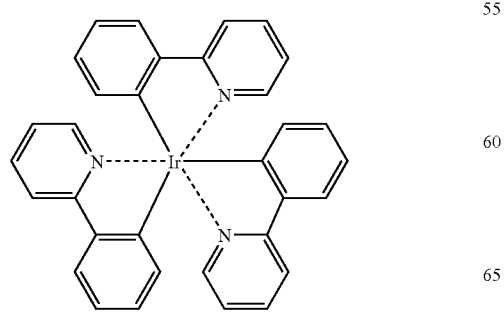

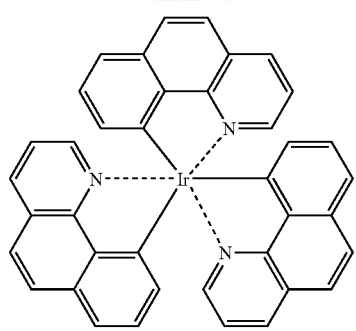
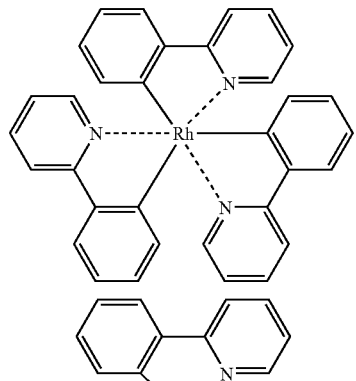
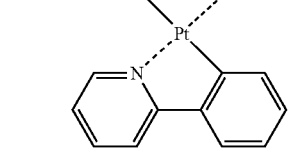
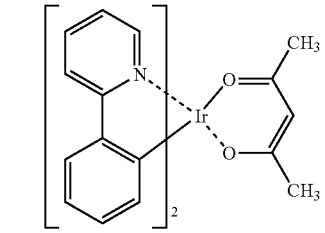
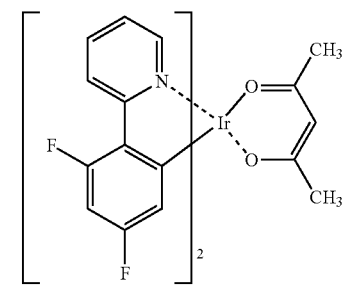
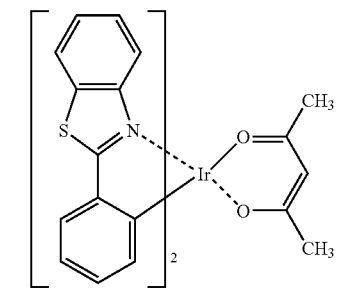
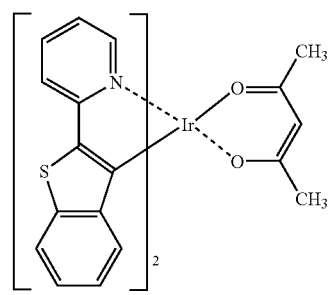
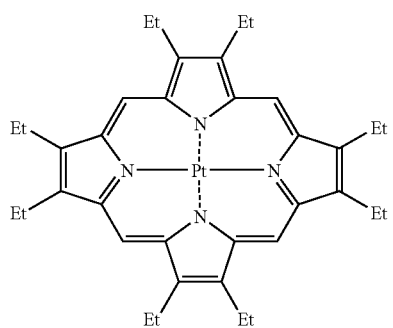
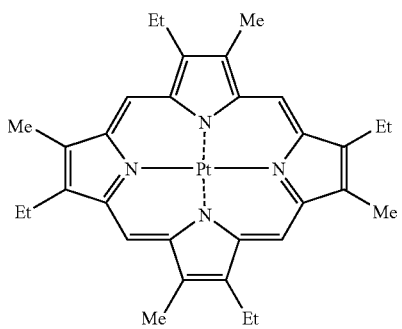
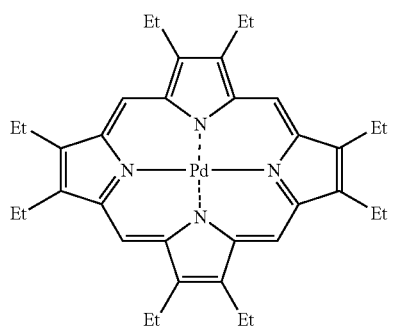
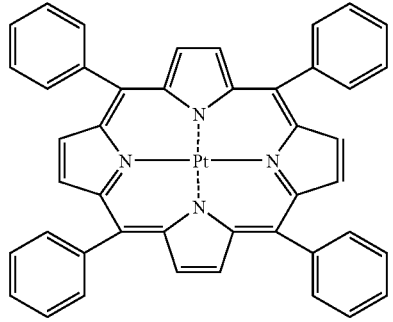

-continued

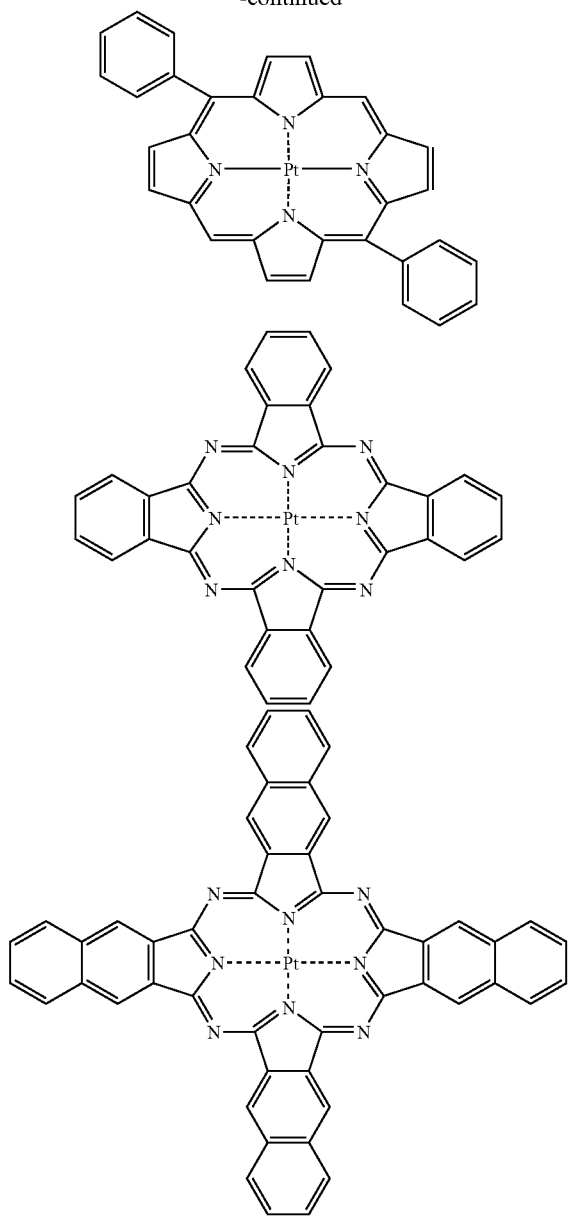

When a phosphorescent dopant is incorporated in the light-emitting layer, the content of the dopant is preferably in the range of 5 to 10 wt %.

BRIEF DESCRIPTION OF THE DRAWING

FIG. 1 schematically shows the cross section of an organic EL device.

EXPLANATION OF SYMBOLS

1 Substrate, 2 anode, 3 hole-injecting layer, 4 hole-transporting layer, 5 light-emitting layer, 6 electron-transporting layer, 7 cathode.

PREFERRED EMBODIMENTS OF THE INVENTION

The organic El device of this invention is described with reference to the drawing, but it is by no means limited in structure to the one shown in the drawing.

FIG. 1 schematically shows the cross section of an organic EL device in general use and the numerals denote the following; 1 substrate, 2 anode, 3 hole-injecting layer, 4 hole-transporting layer, 5 light-emitting layer, 6 electron-transporting layer, and 7 cathode. Preferably, the organic EL device comprises the substrate, anode, hole-transporting layer, light-emitting layer, electron-transporting layer, and cathode as essential layers. Thus, the hole-injecting layer 3 may be omitted and, if necessary, other layers such as a hole-blocking layer may be added.

It is possible to stack the layers in the reverse order to that in FIG. 1; that is, the cathode 7, the electron-transporting layer 6, the light-emitting layer 5, the hole-transporting layer 4, and the anode 2 are stacked in this order on the substrate 1. It is also possible to provide the organic EL device of this invention between two substrates at least one of which is highly transparent.

The organic EL device of this invention is applicable to a single device, a device with a structure arranged in array, or a device with a structure in which the anode and the cathode are arranged in the form of X-Y matrix.

EXAMPLES

This invention is described in more detail below with reference to the accompanying examples, but is not limited to these examples. The number assigned to the compound in the examples corresponds to the number assigned to the chemical formula of a preferable example of the organic metal complexes of this invention.

Example 1

To a 100-ml three-necked flask which had been deaerated and filled with nitrogen were placed 3.0 g of aluminum tri-isopropoxide and 6.2 g of 2-(2-hydroxyphenyl)benzoxazole, 50 ml of anhydrous toluene was added, and the resulting solution was then heated to 60° C. and stirred for 30 minutes. To this solution was added slowly in drops a solution of 3.8 g of 4-diphenylaminophenol in 50 ml of anhydrous toluene and the mixture was stirred at 60° C. for 3 hours. The reaction mixture was cooled to room temperature, the white precipitate formed was filtered off, and the filtrate was concentrated until its volume was reduced to half. The crystals precipitated in the concentrated filtrate were separated by filtration, washed with toluene, and dried under reduced pressure to give 9.0 g of a yellow powder (Compound 1; M=Al). A portion of this powder was purified by sublimation and used in the fabrication of a device.

Compound 1 showed a mass of 708 in an EI-MS measurement and a melting point of 274° C.

Example 2

Compound 1 and Ir(ppy)3 were co-deposited on a glass substrate from different evaporation sources by the vacuum deposition technique at a degree of vacuum of $4.0 \times 10^{-4}$ Pa to form a 50 nm-thick film containing 7.0% of Ir(ppy)3 at a rate of 1.0 Å/sec.

The thin film thus formed was evaluated with the aid of an apparatus for measuring fluorescence. The excitation wavelength was the maximum absorption wavelength of Compound 1 and the light emitted under this condition was observed. Light was emitted not from the host but from the dopant.

Comparative Example 1

A thin film was prepared and evaluated as in Example 2 with the exception of using Alq3 in place of Compound 1 as the main component of the thin film. Emission of light was observed from the host, but not from the dopant.

Example 3

An organic EL device having the structure shown in FIG. 1 less the hole-injecting layer and plus an electron-injecting layer was fabricated. Applying the vacuum deposition technique at a degree of vacuum of $4.0 \times 10^{-4}$ Pa, constituent layers were stacked in thin film one upon another on a glass substrate on which a 150 nm-thick ITO anode had been formed.

At first, a 60 nm-thick film of NPB was formed as a hole-transporting layer on the ITO anode. Then, Compound 1 and Ir(ppy)3 were evaporated from different sources and co-deposited on the hole-transporting layer to form a 25 nm-thick light-emitting layer. The concentration of Ir(ppy)3 there was 7.0%. Next, a 50 nm-thick film of Alq3 was formed as an electron-transporting layer. Thereafter, a 0.5 nm-thick film of lithium fluoride (LiF) was formed on the electron-transporting layer as an electron-injecting layer. Finally, an aluminum electrode with a thickness of 170 nm was formed on the electron-injecting layer.

The organic EL device thus fabricated was connected to an external power source and direct current voltage was applied. The luminous characteristics shown in Table 1 were confirmed. In Table 1, the values of the brightness, voltage, and luminous efficiency are those observed at 10 mA/cm$^2$. The maximum wavelength of the emission spectrum of the device is 517 nm and this indicates that light is emitted from Ir(ppy)3.

Comparative Example 2

An organic EL device was fabricated as in Example 3 with the exception of using HMTPD for the hole-transporting layer and TAZ as the main component of the light-emitting layer.

Comparative Example 3

An organic EL device was fabricated as in Example 3 with the exception of using TAZ as the main component of the light-emitting layer.

TABLE 1

| | Brightness (cd/m$^2$) | Voltage (V) | Luminous efficiency (lm/W) |
| --- | --- | --- | --- |
| Example 3 | 2279 | 8.9 | 8.1 |
| Comparative example 2 | 2050 | 13.2 | 4.9 |
| Comparative example 3 | 1270 | 9.5 | 4.2 |

INDUSTRIAL APPLICABILITY

The organic EL device of this invention emits light of high brightness at high efficiency by application of low voltage. In consequence, the organic EL device of this invention is applicable to flat panel displays (for example, office computers and wall-hanging television sets), vehicle display devices, cellular phone displays, light sources utilizing the characteristics of planar light emitters (for example, light sources of copiers and backlight sources of liquid crystal displays and instruments), signboards, beacon lights, and the like.

What is claimed is:

1. An organic electroluminescent device containing an organic layer comprising an organic metal complex represented by the following general formula (I) for use in an organic EL device:

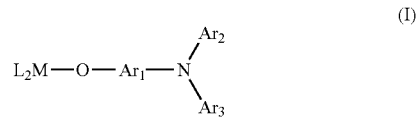

in general formula (I), $Ar_1$ denotes a divalent aromatic hydrocarbon group or a divalent heteroaromatic group and may have substituents;

$Ar_2$ and $Ar_3$ respectively denote an aromatic hydrocarbon group or a heteroaromatic group and may have substituents and $Ar_2$ and $Ar_3$ never link together to form a ring;

M denotes a trivalent metal; and L is a ligand represented by the following general formula (III):

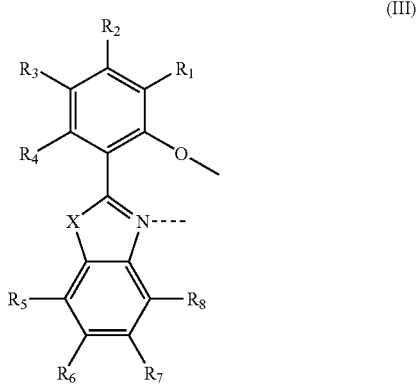

in general formula (III), the groups $R_1$ to $R_8$ respectively denote a hydrogen atom or an arbitrary substituent, substituents located adjacently may link together to form a ring, and X denotes an oxygen or sulfur atom, wherein the organic layer comprising the organic metal complex is a light emitting layer, wherein the organic metal complex is a host material and wherein the host material is doped with a phosphorescent dopant, wherein the aromatic hydrocarbon group of $Ar_2$ and $Ar_3$ is each independently at least one selected from the group consisting of phenyl, naphthyl, acenaphthyl, and anthryl groups, and wherein the heteroaromatic group of $Ar_2$ and $Ar_3$ is each independently at least one selected from the group consisting of pyridyl, quinolyl, thienyl, carbozolyl, indolyl, and furyl groups, wherein the aromatic hydrocarbon group and the heteroaromatic group may be substituted with at least one unsubstituted substituent selected from the group consisting of lower alkyl group of 1 to 6 carbon atoms, lower alkoxy group of 1 to 6 carbon atoms, phenoxy group, methylphenyloxy group, benzyloxy group, phenyl group, naphthyl group, and dimethylamino group.

2. An organic electroluminescent device as described in claim 1, wherein L is a ligand represented by the following general formula (IV):

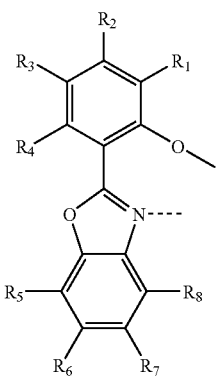 (IV)

in general formula (IV), the groups $R_1$ to $R_8$ individually denote a hydrogen atom, halogen atom, alkyl group, aralkyl group, alkenyl group, alkynyl group, cyano group, dialkylamino group, diarylamino group, diaralkylamino group, amino group, nitro group, acyl group, alkoxycarbonyl group, carboxyl group, alkoxyl group, alkylsulfonyl group, haloalkyl group, hydroxyl group, amide group, aromatic hydrocarbon group which may have substituents, or heteroaromatic group which may have substituents.

3. An organic electroluminescent device as described in any one of claims 1 and 2 wherein $Ar_1$ is represented by the following general formula (IX):

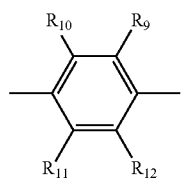 (IX)

in general formula (IX), the groups $R_9$ to $R_{12}$ independently denote a hydrogen atom, halogen atom, alkyl group, aralkyl group, alkenyl group, alkynyl group, cyano group, dialkylamino group, diarylamino group, diaralkylamino group, amino group, nitro group, acyl group, alkoxycarbonyl group, carboxyl group, alkoxyl group, alkylsulfonyl group, haloalkyl group, hydroxyl group, amide group, aromatic hydrocarbon group which may have substituents, or heteroaromatic group which may have substituents, and substituents which are located adjacently may link together to form a ring.

4. An organic electroluminescent device as described in claim 1, wherein the M is an aluminum, gallium or indium.

* * * * *